United States Patent [19]

Rodder

[11] 3,949,739

[45] Apr. 13, 1976

[54] SPIROMETER

[76] Inventor: Jerome A. Rodder, 775 Sunshine Drive, Los Altos, Calif. 94022

[22] Filed: Dec. 11, 1974

[21] Appl. No.: 531,554

[52] U.S. Cl. .............................. 128/2.08; 73/194 R
[51] Int. Cl.² .......................................... A61B 5/08
[58] Field of Search ................ 128/2.08, 2.07, 2 C; 272/57 F; 73/194 R, 205 R, 205 L

[56] References Cited
UNITED STATES PATENTS

| 3,343,413 | 9/1967 | South et al. ...................... 73/194 R |
| 3,395,699 | 8/1968 | Beasley ............................. 128/2.08 |
| 3,403,556 | 10/1968 | Koester ............................. 128/2.08 |
| 3,429,323 | 2/1969 | Mott .................................. 73/194 R |
| 3,709,213 | 1/1973 | Yard .................................. 128/2.08 |
| 3,735,752 | 5/1973 | Rodder ............................. 128/2.08 |
| 3,817,238 | 6/1974 | Matson ............................. 128/2.08 |

FOREIGN PATENTS OR APPLICATIONS 1,518,845   2/1968   France ............................. 73/194 R Primary Examiner—William E. Kamm
Assistant Examiner—Lee S. Cohen
Attorney, Agent, or Firm—Christie, Parker & Hale

[57] ABSTRACT

A spirometer has a source of bias gas directly connected to a flow measurement passage so part of the bias gas flows through the flow measurement passage to the atmosphere instead of flowing through a breath transmission passage. In one embodiment, gas storage chamber is disposed between the breath transmission passage and the flow measurement passage so the gas stored in the chamber enters the flow measurement passage before a patient's breath from the breath transmission passage; the source of bias gas supplies the storage chamber. In another embodiment, a T-network has a first branch conduit connected to the source of gas, a second branch conduit connected to the breath transmission passage, and a third branch conduit connected to the atmosphere; the third branch conduit serves as the flow measurement passage.

16 Claims, 4 Drawing Figures

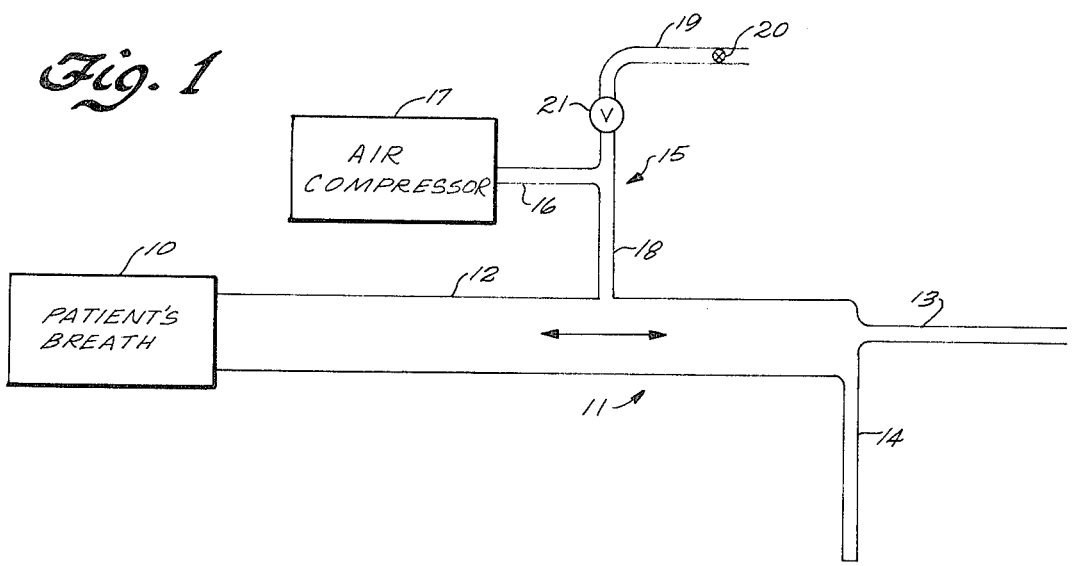
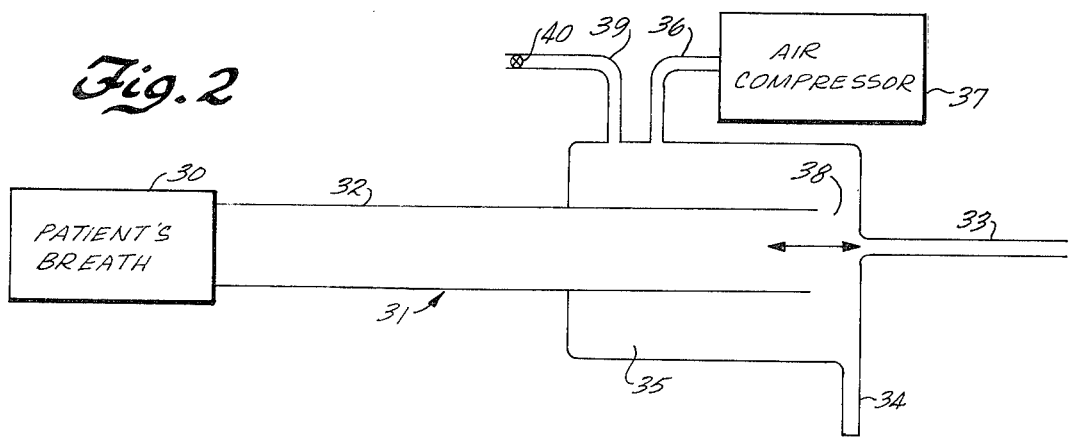
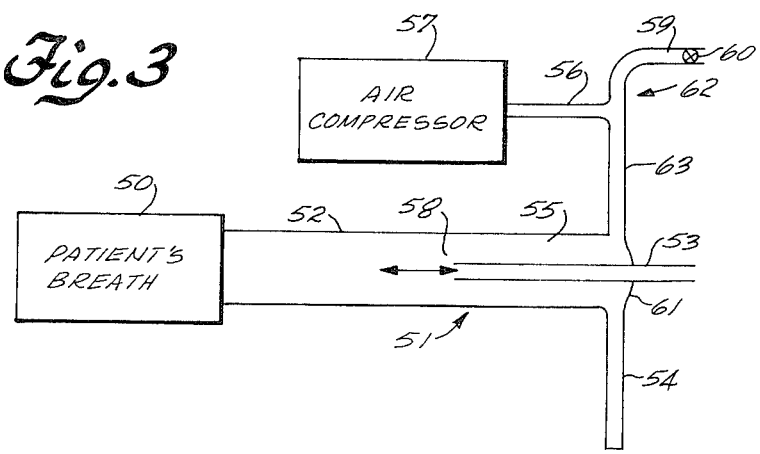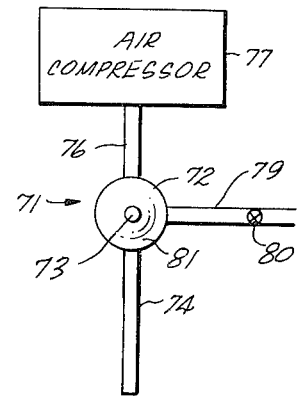

SPIROMETER

BACKGROUND OF THE INVENTION

This invention relates to apparatus for measuring gas flow rate, and more particularly, to such apparatus especially well suited for use as a spirometer.

My U.S. Pat. No. 3,735,752 which issued May 29, 1973, discloses a spirometer comprising a breath transmission passage in which a venturi is formed, and a flow measurement passage that communicates at one end with the throat of the venturi and at the other end with the atmosphere. Air flow through the breath transmission passage creates a subatmospheric pressure at the throat of the venturi to aspirate air from the atmosphere through the flow measurement passage. Apparatus such as a thermistor bead or a hot wire electrically connected into one arm of a bridge circuit measures the flow rate through the flow measurement passage, which is dependent upon the flow rate through the breath transmission passage. Bias air is preferably supplied to the breath transmission passage to insure that the moisture from the patient's breath does not reach the flow rate measuring apparatus in the flow measurement passage. Such moisture would have a deleterious affect on the accuracy of the measurement and would corrode a hot wire.

In the described spirometer, the flow of breath through the breath transmission passage draws air from the atmosphere through the flow measurement passage irrespective of the direction of flow through the breath transmission passage to cool the hot wire or thermistor. As a result, the electrical output from the bridge circuit does not distinguish between inhalation and exhalation.

SUMMARY OF THE INVENTION

According to the invention, a spirometer has a flow measurement passage connected to a breath transmission passage in a manner that permits flow rate measuring apparatus to distinguish between inhalation and exhalation without exposing such apparatus to moisture from the patient's breath. Specifically, a source of bias gas provides the gas flowing through the flow measurement passage; the source is directly coupled to the flow measurement passage so part of the bias gas flows through the flow measurement passage to the atmosphere, instead of flowing through the breath transmission passage. The proportion of the bias gas flowing through the flow measurement passage depends upon whether the patient is exhaling or inhaling, as well as the flow rate of the patient's breath.

In one embodiment of the invention, a gas storage chamber is disposed between the breath transmission passage and the flow measurement passage so the gas stored in the chamber enters the flow measurement passage before breath from the breath transmission passage. The capacity of the gas storage chamber is greater than the patient's anticipated exhalation. In the preferred embodiment, the breath transmission passage comprises a first tube having a large diameter and a second tube having small diameter, a portion of which extends partially into the first tube to form therebetween an annular region comprising the gas storage chamber. The source of bias gas and the flow measurement passage both communicate directly with the gas storage chamber.

In another embodiment of the invention, the breath transmission passage, the flow measurement passage, and the source of bias gas are connected by a T-network having first, second, and third branch conduits. Specifically, the source of bias gas is connected to the first branch conduit, a point intermediate the ends of the breath transmission passage is connected to the second branch conduit, and the third branch conduit which serves as the flow rate measurement passage, is connected to the atmosphere. If desired, the T-network can be employed with the gas storage chamber, in which case the breath transmission passage is connected to the second conduit via the gas storage chamber.

BRIEF DESCRIPTION OF THE DRAWING

The features of specific embodiments of the best mode contemplated of carrying out the invention are illustrated in the drawing, in which:

FIG. 1 is a schematic diagram of an embodiment of the invention employing a T-network;

FIG. 2 is a schematic diagram of an embodiment of the invention employing a gas storage chamber;

FIG. 3 is a schematic diagram of an embodiment of the invention employing a T-network and a gas storage chamber; and FIG. 4 is a schematic diagram of another embodiment of the invention employing a gas storage chamber.

DETAILED DESCRIPTION OF THE SPECIFIC EMBODIMENTS

In FIG. 1, a patient's breath, represented by a block 10, is applied to one end of a breath transmission passage 11, which comprises a tube 12 having a large diameter, and a tube 13 having a small diameter. At one end, tubes 12 and 13 are joined to form a restriction in breath transmission passage 11. At the other end, tube 12 communicates with a patient's breath, and tube 13 communicates with the atmosphere. At the junction of tube 12 and 13, a tubular moisture trap 14 extends vertically downward. Moisture collected in trap 14 is removed by opening a plug, not shown. A T-network 15 has a branch conduit 16 connected to an air compressor 17, which serves as a source of bias gas, a branch conduit 18 connected to an intermediate point along tube 12, and a branch conduit 19 connected to the atmosphere. Compressor 17 is regulated to supply a constant rate of air flow into conduit 16. Flow measurement apparatus 20 is disposed in branch conduit 19, which serves as a flow measurement passage. Apparatus 20 could comprise a thermistor or a hot wire connected in a bridge circuit, as disclosed in FIG. 2 of my U.S. Pat. No. 3,735,752, the disclosure of which is incorporated herein by reference. A needle valve 21 controls the proportion of bias air from compressor 17 that flows through branch conduit 19. Valve 21 is adjusted to the pressure in branch conduit 18 is larger than the pressure in tube 12 when the patient exhales, thereby preventing the flow of the patient's breath through branch conduits 18 and 19 to contaminate apparatus 20. On the other hand, valve 21 is adjusted so that the flow rate through branch conduit 19 is not so high as to cause turbulence therein.

In operation, when the patient exhales, the pressure in tube 12 rises and the proportion of bias air from compressor 17 passing through branch conduit 19, vis-a-vis through branch conduit 18, increases. Conversely, when the patient inhales, the pressure in tube 12 drops and the proportion of bias air from compressor 17 passing through branch conduit 19, vis-a-vis, through branch conduit 18, decreases. Thus, the electrical output of the bridge circuit associated with apparatus 20 distinguishes between exhalation and inhalation, because the hot wire or thermistor is cooled at different rates as the bias air passing through conduit 19 increases and decreases.

In FIG. 2, a breath transmission passage 31 comprises a tube 32 having a large diameter, and a tube 33 having a small diameter. At one end, tubes 32 and 33 are spaced from each other to form an annular slot 38. At the other end, tube 32 communicates with a patient's breath, represented by a block 30, and tube 33 communicates with the atmosphere. A cylindrical gas storage chamber 35 is coaxially disposed about tube 32 at the one end, and tube 33 extends outwardly from chamber 35. As a result, breath transmission passage 31 communicates with gas storage chamber 35 through slot 38. A conduit 36 couples an air compressor 37 to the opposite end of gas storage chamber 35 from slot 38. A conduit 39, which serves as the flow measurement passage, is connected between the end of gas storage chamber 35 opposite slot 38 and the atmosphere. Flow rate measuring apparatus 40 is disposed in conduit 39. A tubular moisture trap 34 extends vertically downward from the bottom at the same end of chamber 35 as slot 38.

When no breath is flowing through breath transmission passage 31, gas storage chamber 35 is filled with clean air from compressor 37, which escapes to the atmosphere through conduit 39 and tube 33. When the patient exhales into breath transmission passage 31, the pressure at slot 38 rises and more of the air in gas storage chamber 35 flows through conduit 39. During exhalation of the patient's breath, it is the clean air in gas storage chamber 35 rather than the patient's breath that flows through conduit 39. In essence, the air stored in chamber 35 serves as a buffer between slot 38 and conduit 39 to prevent the patient's breath from reaching conduit 39 during exhalation. The flow rate of clean air from tube 36 into storage chamber 35 is adjusted so that none of the patient's breath reaches tube 39. To minimize the volume of the gas storage chamber and turbulence in the hot wire cavity, the flow rate in the larger tube 33 is about 100 times that in tube 39.

In FIG. 3, a breath transmission passage 51 comprises a tube 52 having a large diameter, and a tube 53 having a small diameter. One end of tube 53 extends into tube 52, and the other end of tube 53 communicates with the atmosphere. One end of tube 52 communicates with a patient's breath, represented by a block 50, and the other end of tube 52 is closed by an end wall 61, which surrounds tube 53. A tubular moisture trap 54 extends vertically downward from the bottom of tube 52 at end 61. The annular space between tubes 52 and 53 defines a gas storage chamber 55. The space between tube 52 and the end of tube 53 within tube 52 defines an annular slot 58 through which tube 52 communicates with gas storage chamber 55. The configuration of gas storage chamber 55 and annular slot 58 is preferable to the configuration in FIG. 1 because less turbulance is created at high flow rates and the storage chamber 55 allows for a reduction in the bias air flow rate. A T-network 62 comprises a branch conduit 56 connected to an air compressor 57, a branch conduit 63 connected to tube 52 at end 61, and a branch conduit 59 that communicates with the atmosphere. Flow rate measuring apparatus 60 is disposed in branch conduit 59. At high flow rates, the placement of conduit 18 in the middle of tube 12 (FIG. 1) creates turbulence in conduits 18 and 19, which impairs accurate flow measurement. Such turbulence is avoided by placing tube 63 at the end of gas storage chamber 55, where less flow occurs.

When no breath flows through breath transmission passage 51, bias air from compressor 57 fills gas storage chamber 55. When a patient exhales into breath transmission passage 51, the air flow rate through conduit 59 to the atmosphere increases, and when a patient inhales from breath transmission passage 51, the flow rate through conduit 59 to the atmosphere decreases. In this embodiment, it is not necessary that the pressure in conduit 63 be greater than the pressure at annular slot 58 during exhalation, because the clean air from compressor 57 stored in chamber 55 flows through conduit 59 before the patient's breath, which is exhausted before all the air in gas storage chamber 55 flows through conduit 59.

FIG. 4 is an end view of an arrangement identical to that of FIG. 3, except that the bias air and the flow rate measuring apparatus are separately coupled to the gas storage chamber. Thus, a breath transmission passage 71 comprises a tube 72 having a large diameter, and a tube 73 having a small diameter. One end of tube 73 extends into tube 72, the other end of tube 73 communicates with the atmosphere. An end wall 81 covers one end of tube 72 and the other end of tube 72 communicates with a patient's breath. A tubular moisture trap 74 extends downwardly from tube 72 at end wall 81. The annular region between tube 72 and the portion of tube 73 extending into tube 72 forms a gas storage chamber. A conduit 76 connects an air compressor 77 to the storage chamber at end 81. A conduit 79 connects the gas storage chamber at end 81 to the atmosphere. Flow rate measuring apparatus 80 is disposed in conduit 79.

A typical diameter for tubes 12, 32, 52, and 72 would be 20 mm; a typical diameter for tubes 13, 33, 53, and 73 would be between 12 and 15 mm; and a typical diameter for conduits 16, 18, 19, 36, 39, 56, 59, 63, 76, and 79 would be between 3 and 4 mm. Typically, air compressors 17, 37, 57, and 77 would provide bias air at a constant flow rate between 10 and 200 cubic centimeters per minute.

The arrangement of FIG. 1 is suitable for use at low flow rates, i.e., in the range of 0 to 200 liters per minute, the arrangement of FIG. 3 is suitable for high flow rates, i.e., in the range of 0 to 500 liters per minute, and the arrangement of FIG. 2 and FIG. 4 is suitable for a range of high and low flow rates, i.e., 0 to 1000 liters per minute (exhalation only).

The present invention can be used to advantage with the flow rate measuring apparatus disclosed in my copending application entitled "Fluid Measuring Apparatus," Ser. No. 523,995, filed on Nov. 15, 1974. In such case, conduit 19, conduit 39, conduit 59, and conduit 79 would be connected to conduit 52 of the referenced copending application.

The described embodiment of the invention is only considered to be preferred and illustrative of the inventive concept; the scope of the invention is not to be restricted to such embodiment. Various and numerous other arrangements may be devised by one skilled in the art without departing from the apirit and scope of this invention.

What is claimed is:

1. A spirometer comprising:
   a breath transmission passage having a first end and a second end that are open, the first end being adapted for communication with the breath of a patient and the second end being adapted for communication with the atmosphere;
   a flow measurement passage communicating with the atmosphere at one end;
   a source of gas under pressure;
   means for coupling the source of gas to the breath transmission passage and the flow measurement passage so part of the gas flows through the flow measurement passage to the atmosphere without flowing through the breath transmission passage, the proportion of gas flowing through the flow measurement passage increasing during exhalation and decreasing during inhalation; and
   means for measuring the gas flow rate through the flow measurement passage.

2. The spirometer of claim 1, in which the coupling means comprises a gas storage chamber disposed between the breath transmission passage and the flow measurement passage so the gas stored in the chamber enters the flow measurement passage before breath from the breath transmission passage, and means for connecting the source of gas to the storage chamber.

3. The spirometer of claim 2, in which the means for connecting the source of gas to the storage chamber comprises a conduit connected between the source of gas and the storage chamber.

4. The spirometer of claim 3, in which the breath transmission passage comprises a first tube having a large diameter adapted for communication with a patient's breath, and a second tube having a small diameter adapted for communication with the atmosphere, the first and second tubes being longitudinally spaced from each other to form an annular slot, and the storage chamber surrounds the tubes at the slot to provide communication between the breath transmission passage and the flow measurement passage.

5. The spirometer of claim 3, in which the breath transmission passage comprises a first tube having a large diameter adapted for communication with the patient's breath, a second tube having a small diameter adapted for communication with the atmosphere, the second tube extending partially into the first tube to form an annular region therebetween, and means for closing the end of the first tube where the second tube extends therein; the storage chamber comprises the annular region and the conduit is connected to the storage chamber at the closed end of the first tube.

6. The spirometer of claim 2, in which the means for connecting the source of gas to the storage chamber comprises a conduit connected between the source of gas and the flow measurement passage.

7. The spirometer of claim 6, in which the breath transmission passage comprises a first tube having a large diameter adapted for communication with the patient's breath, a second tube having a small diameter adapted for communication with the atmosphere, the second tube extending partially into the first tube to form an annular region therebetween, and means for closing the end of the first tube where the second tube extends therein, the storage chamber comprising the annular region, and the flow measurement passage is connected to the storage chamber at the closed end of the first tube.

8. The spirometer of claim 1, in which the coupling means comprises a conduit connected between the source of gas and the flow measurement passage and means for connecting the flow measurement passage at the other end to the breath transmission passage.

9. The spirometer of claim 8, in which the breath transmission passage comprises a first tube having a large diameter adapted for communication with the patient's breath, a second tube having a small diameter adapted for communication with the atmosphere, the second tube extending partially into the first tube to form an annular region therebetween, and means for closing the end of the first tube where the second tube extends therein.

10. The spirometer of claim 9, in which the flow measurement passage is connected to the breath transmission passage at the closed end of the first tube.

11. The spirometer of claim 1, in which the breath transmission passage comprises a first tube having a large diameter adapted for communication with a patient's breath, and a second tube having a small diameter adapted for communication with the atmosphere and connected to the first tube, additionally comprising a moisture trap in the first tube at a low point.

12. The spirometer of claim 1, in which the flow rate measuring means comprises a resistive element having a resistance related to its temperature disposed in the flow measurement passage in heat transfer relationship with gas flowing through the flow measurement passage, a source of electrical energy connected to the resistive element to heat the resistive element; and means for sensing changes in resistance of the resistive element.

13. The spirometer of claim 1, in which the coupling means comprises a T-network having first, second, and third branch conduits, the source of gas being connected to the first branch conduit, the second branch conduit being connected to the breath transmission passage at a point intermediate to the first and second ends, and the third branch conduit being connected to the atmosphere to serve as the flow measurement passage.

14. The spirometer of claim 13, in which the flow rate measuring means comprises a resistive element having a resistance related to its temperature disposed in the third branch conduit in heat transfer relationship with gas flowing through the flow measurement passage, a source of electrical energy connected to the resistive element to heat the resistive element; and means for sensing changes in resistance of the resistive element.

15. The spirometer of claim 13, in which the coupling means additionally comprises a gas storage chamber between the second branch conduit and the breath transmission passage, the gas storage chamber having a gas storage capacity greater than the amount of breath exhaled by a patient.

16. The spirometer of claim 15, in which the breath transmission passage comprises a first tube having a large diameter adapted for communication with the patient's breath, a second tube having a small diameter adapted for communication with the atmosphere, the second tube extending partially into the first tube to form therebetween an annular region, and means for closing the end of the first tube where the second tube extends therein, the storage chamber comprising the annular region and the second branch conduit being connected to the annular region at the closed end of the first tube.

* * * * *